United States Patent [19]

Black

[11] 4,011,828
[45] Mar. 15, 1977

[54] RESPIRATORY SIGNALLING DEVICE

[75] Inventor: Geoffrey Donald Black, Sawbridgeworth, England

[73] Assignee: The Medishield Corporation Limited, London, England

[22] Filed: Oct. 1, 1975

[21] Appl. No.: 618,356

[30] Foreign Application Priority Data

Oct. 1, 1974 United Kingdom ............ 42625/74

[52] U.S. Cl. .......................... 116/70; 128/DIG. 29
[51] Int. Cl.² ................... A62B 7/00; G01L 19/12
[58] Field of Search .......................... 116/65, 70; 128/DIG. 29, 2 R, 2.08, 145.8

[56] References Cited
UNITED STATES PATENTS

| 859,147 | 7/1907 | Strodtbeck | 128/2 R X |
| 2,777,251 | 1/1957 | Bailey | 116/65 X |
| 2,905,136 | 9/1959 | Jukes | 116/70 |
| 3,870,012 | 3/1975 | Metivier | 128/DIG. 29 X |
| 3,898,987 | 8/1975 | Elam | 116/70 X |
| 3,946,729 | 3/1976 | Hanna | 128/DIG. 29 |

Primary Examiner—Richard C. Queisser
Assistant Examiner—Daniel M. Yasich
Attorney, Agent, or Firm—Dennison, Dennison, Meserole & Pollack

[57] ABSTRACT

A device including a chamber having two inlets and an outlet. One inlet is connected to an expiratory valve in a lung ventilator or like machine, the other inlet is in communication with a whistle and the outlet is connected to an aspirator. The device gives an intermittent audible signal when the ventilator is operating and saves the operator of the ventilator from having to look at the expiratory valve thereof to verify its correct operation.

6 Claims, 1 Drawing Figure

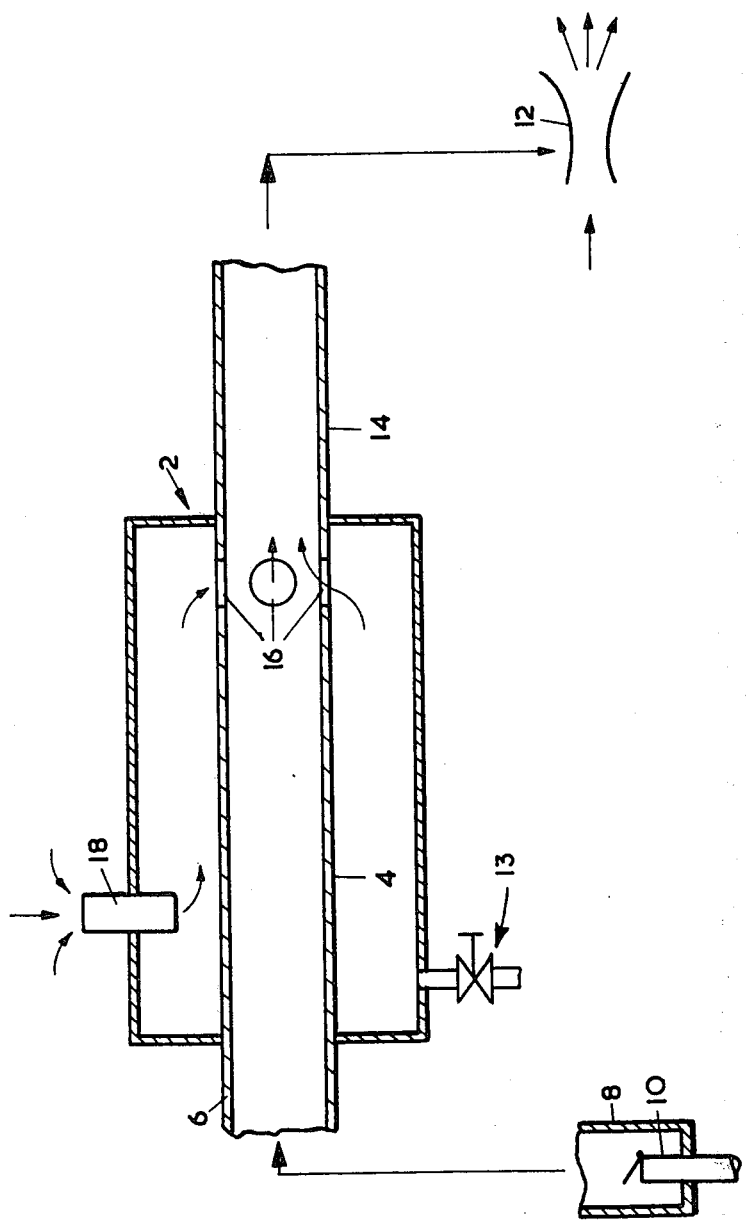

RESPIRATORY SIGNALLING DEVICE

This invention relates to a respiratory signalling device intended to be used to indicate the correct operation (and conversely, the malfunctioning) of the patient breathing circuit in anaesthetic apparatus or like machines for assisting the breathing of a patient.

One of the problems associated with administering volatile or gaseous anaesthetics to a patient is the disposal of the gases expelled by the patient. It is undesirable that these gases are vented into the atmosphere of the operating theatre, for obvious reasons, as they can, in the long term, be harmful to the health of the theatre staff.

It has been proposed that this problem be overcome by connecting a conduit to the expiratory valve of a breathing circuit, so that all gases emitted through the valve are led outside the theatre, to be vented safely. This has the side-effect of acoustically insulating the expiratory valve. The anaesthetist or surgeon is therefore no longer able to hear the sound of the valve operating, which is unfortunate since the sound provides a valuable safeguard in that the anaesthetist can hear whether or not the equipment is operating normally and he need not look at the equipment or the patient to verify that respiration is satisfactory.

The present invention aims at providing means for producing an intermittent signal related to the operation of the expiratory valve of an anaesthetic breathing circuit or like machine for assisting breathing of a patient.

Accordingly the present invention provides a respiratory signalling device which is as claimed in the appended claims.

The present invention will now be described by way of example with reference to the accompanying drawing, which is a diagrammatic view of one form of apparatus of the present invention.

The device of the present invention includes a casing 2 through which passes a conduit 4. The inlet end 6 of conduit 4 is adapted to be connected, in use, to a shroud 8 enclosing a Heidbrink or other expiratory valve 10 shown only diagrammatically. The valve 10 is designed to be one-way in operation so that gas passes through it into the interior of shroud 8 only after it has been exhaled by the patient. This exhaled gas then passes along conduit 4 and flows to an aspirator or suction-producing device 12 of conventional construction (shown only diagrammatically as a venturi) connected to the outlet 14 of conduit 4. The device 12, which is able to reduce the pressure within the interior of conduit 4 to a pressure slightly below atmospheric, can be of the Venturi or like type or it may be pump driven by an electric motor.

That portion of conduit 4 which is positioned within casing 2 is provided with a series of openings 16 placing the interior of the conduit in communication with the interior of the casing. In a wall of casing 2 is positioned a whistle 18 designed to emit an audible signal when air is induced to flow into the interior of casing 2 by virtue of the sub-atmospheric pressure in casing 2 produced by device 12.

A conventional air-flow control valve 13 can be provided in the wall of the casing 2 to act as a flow shunt so that the flow of air flowing through the whistle or like gas-operated signalling means, and thus the volume of the audible signal emitted thereby, can be regulated.

Another alternative to the valve 13 can take the form of an aperture in the wall of the casing 2 with an associated shutter which can sweep across it to vary its size.

Matters are arranged so that the sub-atmospheric pressure in conduit 4 has a negligible effect on operation of the expiratory valve 10. In particular, the apparatus is intended to reduce the pressure in the patient's lungs by a negligible extent when the suction device 12 is placed in communication with the lungs when valve 10 opens.

The inlet 6 and whistle 18 can be regarded as being differential inlets to suction device 12.

In one mode of operation of the device of the present invention, when the expiratory valve 10 is shut, all the gas flowing through outlet 14 of conduit 4 passes through the whistle 18, which is thus caused to emit an audible signal. When the patient reaches the expiratory portion of the respiratory cycle, the valve 10 opens and the exhaled gases flow through conduit 4 to device 12. This has the effect of reducing significantly the flow of gas through the whistle 18, which is thereby caused to make less sound or become silent. Towards the end of the expiratory phase, the flow of gas exhaled by the patient reduces to such an extent that the concomitant flow of gas to the whistle 18 increases until it is again emitting an audible signal. However, what is important is not that the whistle is quieter during the whole of the expiratory phase of the respiratory cycle, but rather that the audible signal varies with the intermittent operation of the expiratory valve.

Should the suction device 12 fail to operate, whistle 18 will only emit an audible signal during the expiratory phase of the patient's respiratory cycle by passage of the exhaled gases through the series of openings 16 into the casing 2 and thence through whistle 18. Thus, in this form of the device of the invention, the presence of a signal during the expiratory phase of the patient's respiratory cycle acts as an indication that the suction device is not functioning.

Other modifications can of course be made. Thus for example, that portion of conduit 4 positioned within casing 2 can be omitted, with the inlet 6 and outlet 14 being connected directly to the walls of casing 2.

It is also within the ambit of this invention for the whistle 18 to be silent when the flow of gas through it is at a maximum, and to emit noise only when the gas flow has fallen to a lower level. In this way, the whistle can give out a signal concurrently with actuation of the expiratory valve, which tends to reduce noise pollution of the operating theatre.

I claim:

1. In a signalling device for an artificial respirator the combination comprising: a chamber, an outlet in one wall of said chamber adapted to be connected to an aspirator, means defining first and second inlets communicating with the interior of said chamber, fluid flow responsive acoustic signalling means operably connected with one of said first and second inlets and interconnecting the interior of said chamber with said signalling means, shroud means connected to the other of said inlets, a gas pressure responsive expiratory valve selectively connecting the interior of said shroud to an intermittent gas pressure source whereby operation of said expiratory valve in response to variations in said intermittent gas pressure from said source intermittently operates said signalling device.

2. A device as claimed in claim 1, in which said chamber is in the form of a conduit, one end of said conduit acting as said outlet and the other end of said conduit acting as one of said inlets and connected to the interior of said shroud, a casing surrounding said conduit, said conduit having at least one opening connecting its interior with the interior of said casing, said opening acting as the other of said first and second inlets and said gas-operated signalling means is operatively mounted on said casing and communicates with the interior thereof.

3. A device as claimed in claim 1, which also includes a further inlet connected to a variable air-flow control valve whereby adjustment of the said control valve enables the volume of the audible signal emitted by said signalling means to be regulated.

4. A device as claimed in claim 1, in which the acoustic signalling means is a whistle.

5. A device as claimed in claim 1, in which the signalling means is adapted to emit an audible signal during the expiratory phase of a patient's respiratory cycle.

6. A device as claimed in claim 1, in which the signalling means is adapted to emit an audible signal during the inspiratory phase of a patient's respiratory cycle.

* * * * *